US011192845B2

(12) United States Patent
Jung et al.

(10) Patent No.: US 11,192,845 B2
(45) Date of Patent: Dec. 7, 2021

(54) PROCESS FOR HYDROGENATION OF PHTHALATE COMPOUND

(71) Applicant: Hanwha Solutions Corporation, Seoul (KR)

(72) Inventors: Ki Taeg Jung, Daejeon (KR); Hyo Suk Kim, Daejeon (KR); Seong Min Park, Seoul (KR); Hye Won Lee, Daejeon (KR); Jae Heum Jung, Busan (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 0 days.

(21) Appl. No.: 16/763,656

(22) PCT Filed: Nov. 1, 2018

(86) PCT No.: PCT/KR2018/013194
§ 371 (c)(1),
(2) Date: May 13, 2020

(87) PCT Pub. No.: WO2019/107770
PCT Pub. Date: Jun. 6, 2019

(65) Prior Publication Data
US 2020/0283369 A1    Sep. 10, 2020

(30) Foreign Application Priority Data
Nov. 29, 2017    (KR) .................. 10-2017-0161949

(51) Int. Cl.
*C07C 67/303* (2006.01)
*C07C 69/75* (2006.01)
*C08L 101/00* (2006.01)
C08K 5/12 (2006.01)

(52) U.S. Cl.
CPC ............ *C07C 67/303* (2013.01); *C07C 69/75* (2013.01); *C08L 101/00* (2013.01); C08K 5/12 (2013.01)

(58) Field of Classification Search
CPC ....... C07C 67/303; C07C 69/75; C07C 51/36; C08L 101/00; C08K 5/12
See application file for complete search history.

(56) References Cited

U.S. PATENT DOCUMENTS

| | | | | |
|---|---|---|---|---|
| 6,281,388 B1 * | 8/2001 | Goodwin, III | ........ | C07C 209/48 564/492 |
| 7,253,329 B2 * | 8/2007 | Herwig | ..................... | C07C 5/05 585/259 |
| 7,361,714 B2 * | 4/2008 | Grass | ..................... | B01J 23/462 525/338 |
| 7,435,848 B2 * | 10/2008 | Grass | ..................... | C07C 67/303 560/116 |
| 8,946,467 B2 * | 2/2015 | Reine | ..................... | C07C 67/303 560/127 |
| 2006/0161017 A1 * | 7/2006 | Grass | ..................... | C07C 67/303 562/509 |
| 2012/0296111 A1 | 11/2012 | Konigsmann et al. | | |
| 2018/0015450 A1 | 1/2018 | Jung et al. | | |
| 2019/0048167 A1 * | 2/2019 | Kim | ..................... | C08L 23/0853 |
| 2020/0299222 A1 * | 9/2020 | Lee | ..................... | C08K 5/101 |
| 2020/0361846 A1 * | 11/2020 | Kim | ..................... | B01J 23/46 |

FOREIGN PATENT DOCUMENTS

| | | | |
|---|---|---|---|
| CN | 103130648 A | * | 6/2013 |
| CN | 105037161 A | * | 11/2015 |
| EP | 3085686 | | 10/2016 |
| JP | 2013-513477 | | 4/2013 |
| JP | 2016-69587 | | 5/2016 |
| JP | 2016-141729 | | 8/2016 |
| KR | 10-2012-0092197 | | 8/2012 |
| KR | 10-1556340 | | 6/2015 |
| KR | 101556340 B1 | * | 9/2015 |
| KR | 10-2016-0076320 | | 6/2016 |
| KR | 10-2016-0118010 | | 10/2016 |
| KR | 10-1797220 | | 3/2017 |

OTHER PUBLICATIONS

Henry et al, Industrial & Engineering Chemistry Process Design and Development, Scale Up of Pilot Plant Data for Catalytic Hydroprocessing, 1973, 12(3), pp. 328-334. (Year: 1973).*

J Hochman et al., 8 Industrial & Engineering Chemistry Fundamentals, 63-71 (1969) (Year: 1969).*

KIPO, PCT Search Report & Written Opinion of PCT/KR2018/013194 dated Apr. 11, 2019.

EPO, Extended European Search Report of EP 18884221.5 dated Aug. 12, 2021.

* cited by examiner

Primary Examiner — Alexander R Pagano
(74) Attorney, Agent, or Firm — Lex IP Meister, PLLC

(57) ABSTRACT

Provided is a hydrogenation method of a phthalate compound. According to the present invention, in the hydrogenation reaction, generation of by-products is suppressed, and thus catalytic activity is improved and life-time is extended, thereby increasing efficiency of a commercial process and economic efficiency. Further, since the hydrogenation product prepared by the present invention has high purity and a low acid value, its quality as a plasticizer is excellent, thereby being applied to a variety of products.

7 Claims, 1 Drawing Sheet

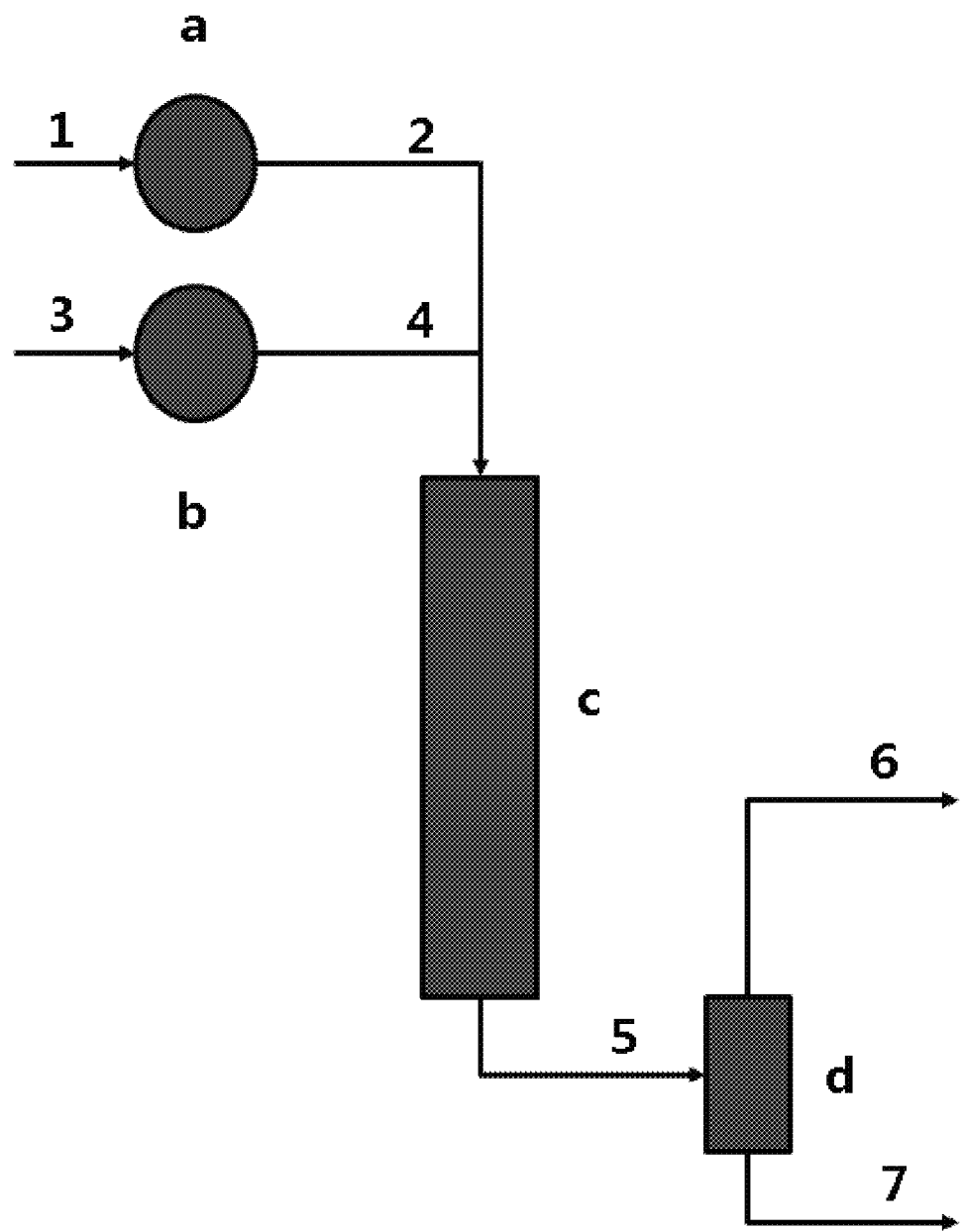

PROCESS FOR HYDROGENATION OF PHTHALATE COMPOUND

CROSS-REFERENCE TO RELATED APPLICATION

The present application is based on, and claims priority from, Korean Patent Application No. 10-2017-0161949, filed on Nov. 29, 2017, the disclosure of which is hereby incorporated by reference herein in its entirety.

TECHNICAL FIELD

The present invention relates to a hydrogenation method of a phthalate compound. Particularly, the present invention relates to a hydrogenation method of a phthalate compound, the method capable of suppressing generation of by-products to extend a life-time of a catalyst as well as maintaining a low acid value of a hydrogenation product to improve its quality as a plasticizer.

BACKGROUND ART

Phthalate-based compounds are materials widely used as plasticizers for plastics, particularly, polyvinyl chloride (PVC). For example, phthalate-based compounds may be used in a wide variety of applications such as electrical and electronic products, medicines, paint pigments, lubricants, binders, surfactants, adhesives, tiles, food containers, package materials, etc.

However, since some of the phthalate compounds have been known to be materials causing environmental pollution and human endocrinal disruption problems, restrictions on use thereof have been tightened in advanced countries such as Europe, the US, etc. Particularly, among phthalate-based plasticizers, some products such as di(2-ethylhexyl) phthalate (DEHP), butyl benzyl phthalate (BBP), and di-n-butyl phthalate (DBP) are suspected to be environmental hormones, that is, endocrine disruptors inhibiting or disrupting hormone actions in the human body, such that there is a trend toward regulation on these products.

For this reason, efforts have been made to develop an eco-friendly plasticizer free from debate in terms of environmental hormones while having performance equal to that of the existing plasticizers. As one of the efforts, there is a method of using a compound which is prepared by hydrogenation of a benzene ring included in a phthalate compound.

As a hydrogenation reaction of an aromatic compound such as a benzene ring, a method of using a catalyst in which a transition metal such as ruthenium is contained as an active ingredient on a support has been known.

However, the transition metal catalyst has a problem in that its activity rapidly decreases while the reaction proceeds, resulting in a yield reduction. Accordingly, efforts have been continued to solve the problems of the hydrogenation reaction for improvement of productivity and economic efficiency of the process. For example, Korean Patent No. 1556340 discloses a hydrogenation method of reacting a phthalate compound with hydrogen in the presence of a hydrogenation catalyst and an alcohol, whereby performance and life-time of the catalyst are improved.

Meanwhile, the hydrogenation reaction entails side reactions. As the content of by-products increases, the manufactured product becomes acidic. If an acid value of the product exceeds a certain level, an odor is produced and purity decreases, resulting in generation of quality problems as a plasticizer. Moreover, the by-products also lower activity of the hydrogenation catalyst, and accordingly, there is a need for a novel hydrogenation method of a phthalate compound capable of suppressing generation of by-products in order to improve productivity and economic efficiency of the process and to improve quality of the product.

PRIOR ART DOCUMENT

Patent Document 1: Korean Patent No. 1556340, "Hydrogenation method of phthalate compound"

DISCLOSURE

Technical Problem

The present invention has been made to solve the above problems, and an object of the present invention is to provide a novel hydrogenation method of a phthalate compound, the method being capable of improving purity of a product while controlling an acid value of a reaction product by suppressing side reactions and being capable of increasing a reaction yield by improving hydrogenation performance of the phthalate-based compound.

Technical Solution

To achieve the above object, there is provided a hydrogenation method of a phthalate compound, the method including the steps of introducing a gas-phase raw material including hydrogen and a liquid-phase raw material including the phthalate compound into a reactor and allowing a reaction of the hydrogen and the phthalate compound in the presence of a hydrogenation catalyst, wherein the Reynold's number of the liquid-phase raw material is 1 to 100, and an acid value of a hydrogenation product separated after the reaction is 0.3 KOHmg/g or less.

The acid value of the hydrogenation product separated after the reaction is preferably 0.2 KOHmg/g or less.

The acid value of the hydrogenation product separated after the reaction is preferably 0.4 KOHmg/g or less or 0.3 KOHmg/g or less after heating.

The amount of hydrogen introduced into the reactor may be 3 mol to 300 mol with respect to 1 mol of the phthalate compound.

The phthalate compound may be one or more selected from the group consisting of phthalate, terephthalate, isophthalate, and carboxylic acid compounds thereof.

In the hydrogenation method of a phthalate compound of the present invention, the gas-phase raw material may be fed into an upper portion or a lower portion of the reactor, and the liquid-phase raw material may be fed into an upper portion of the reactor.

The active ingredient of the hydrogenation catalyst may be one or more selected from the group consisting of ruthenium (Ru), rhodium (Rh), palladium (Pd), and platinum (Pt), and the hydrogenation catalyst may include 3% by weight or less of the catalyst active ingredient with respect to 100% by weight of a support.

Further, there is provided a hydrogenated phthalate or terephthalate compound prepared by the above method.

The hydrogenated phthalate or terephthalate compound may be used as a plasticizer.

Furthermore, there is provided a resin composition including the plasticizer, and a resin selected from ethylene vinyl acetate, polyethylene, polypropylene, polyvinyl chloride, polystyrene, polyurethane, polybutadiene, silicone, thermoplastic elastomers, and copolymers thereof.

Effect of the Invention

According to a hydrogenation method of a phthalate compound of the present invention, generation of by-products is suppressed to improve catalytic activity and to extend a life-time, thereby increasing efficiency of a commercial process and economic efficiency. Further, since a hydrogenation product prepared by the present invention has high purity and a low acid value, and it has excellent quality as a plasticizer, thereby being applied to various products.

BRIEF DESCRIPTION OF DRAWINGS

The drawing is a schematic illustration of a hydrogenation reaction apparatus used in a hydrogenation method of the present invention.

BEST MODE FOR CARRYING OUT THE INVENTION

The present invention may be variously modified and have various embodiments, and specific embodiments will be exemplified and described in detail. However, the present invention is not limited to the exemplary embodiments described herein, but all of the modifications, equivalents, and substitutions within the spirit and scope of the present invention are also included in the present invention. Further, when it is determined that the detailed description of the known art related to the present invention may obscure the gist of the present invention, the detailed description thereof will be omitted.

In addition, terms including an ordinal number such as first, second, or the like to be used below may be used to describe various components. However, these components are not limited to these terms. The terms are only used to differentiate one component from other components. For example, the 'first' component may be called the 'second' component and the 'second' component may be called the 'first' component, without departing from the scope of the present invention.

Singular forms are intended to include plural forms unless the context clearly indicates otherwise. Terms such as "include", "have", and the like, used in the present specification, will imply the existence of stated features, numbers, steps, operations, configuration elements, components, or a combination thereof, but do not preclude the presence or addition of one or more other features, numbers, steps, operations, configuration elements, components, or a combination thereof.

Hereinafter, a hydrogenation method of a phthalate compound of the present invention will be described in detail with reference to drawings.

According to a preferred embodiment of the present invention, provided is a hydrogenation method of a phthalate compound, the method including the steps of introducing a gas-phase raw material including hydrogen and a liquid-phase raw material including the phthalate compound into a reactor and allowing a reaction of the hydrogen and the phthalate compound in the presence of a hydrogenation catalyst, wherein the Reynold's number of the liquid-phase raw material is 1 to 100, and an acid value of a hydrogenation product separated after the reaction is 0.3 KOHmg/g or less.

In the present invention, generation of by-products may be suppressed by operating while controlling the Reynold's number of the liquid-phase raw material within a specific numerical range. Therefore, the life-time of the hydrogenation catalyst in the reactor may be improved, and it is possible to secure the effects of improving process productivity, yield, and economic efficiency. Further, according to the hydrogenation method of the present invention, the hydrogenation product having an acid value at a predetermined level or less may be prepared, and thus its quality as a plasticizer may be improved.

A reaction target of the hydrogenation method of the present invention is a phthalate compound, and hydrogen is added to a benzene ring of the phthalate compound by the hydrogenation, thereby being converted into a cyclohexane dicarboxylate compound corresponding to the phthalate compound.

The phthalate compound may be one or more selected from phthalate, terephthalate, isophthalate, and a carboxylic acid compound corresponding thereto.

First, the phthalate compound may be represented by the following Chemical Formula 1.

[Chemical Formula 1]

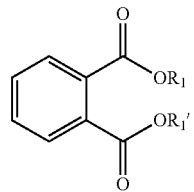

In Chemical Formula 1, R1 and R1' are each independently the same as or different from each other, and are hydrogen, or a straight- or branched-chain alkyl group having 1 to 20 carbon atoms, preferably 4 to 20 carbon atoms, more preferably 5 to 20 carbon atoms, and most preferably 5 to 10 carbon atoms.

Specific examples of the phthalate compound may include dibutyl phthalate (DBP), dihexyl phthalate (DHP), dioctyl phthalate (DOP), di-n-octyl phthalate (DnOP), diisononyl phthalate, diisodecyl phthalate (DIDP), etc., but are not limited thereto. These compounds may be used alone or in a mixture.

The terephthalate compound may be represented by the following Chemical Formula 2.

[Chemical Formula 2]

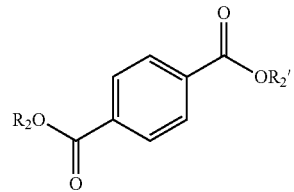

In Chemical Formula 2, R2 and R2' are each independently the same as or different from each other, and are hydrogen, or a straight- or branched-chain alkyl group having 1 to 20 carbon atoms, preferably 4 to 20 carbon atoms, more preferably 5 to 20 carbon atoms, and most preferably 5 to 10 carbon atoms.

Specific examples of the terephthalate compound may include dibutyl terephthalate (DBTP), dioctyl terephthalate (DOTP), diisononyl terephthalate (DINTP), or diisodecyl terephthalate (DIDTP), but are not limited thereto. These compounds may be used alone or in a mixture.

The isophthalate compound may be represented by the following Chemical Formula 3.

[Chemical Formula 3]

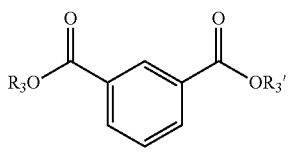

In Chemical Formula 3, R3 and R3' are each independently the same as or different from each other, and are hydrogen, or a straight- or branched-chain alkyl group having 1 to 20 carbon atoms, preferably 4 to 20 carbon atoms, more preferably 5 to 20 carbon atoms, and most preferably 5 to 10 carbon atoms.

Specific examples of the isophthalate compound may include dibutyl isophthalate (DBIP), dioctyl isophthalate (DOIP), diisononyl isophthalate (DINIP), diisodecyl isophthalate (DIDIP), etc., but are not limited thereto. These compounds may be used alone or in a mixture.

Preferably, dioctyl terephthalate (DOTP) may be used as the phthalate compound.

Purity of the phthalate compound may be about 99% or more, preferably about 99.5% or more, and more preferably about 98% or more, but is not limited thereto. Any phthalate compound with commercially available quality and purity may be used.

The hydrogenation process of the phthalate compound may be carried out in a liquid phase or in a gas phase. In the present invention, the phthalate compound is included in the liquid-phase raw material and hydrogen is included in the gas-phase raw material, which are introduced into a reactor filled with a hydrogenation catalyst.

In the present invention, the Reynold's number of the liquid-phase raw material introduced into the reactor may be 1 to 100.

The Reynold's number ($N_{RE}$) is a ratio of "inertial forces" to "viscous forces" of a fluid, and is represented by the following Equation 1:

$$\text{Reynold's No.}(N_{Re}) = \frac{\rho \times u_z \times D_p}{\mu} \quad \text{[Equation 1]}$$

μ: viscosity ρ: density $u_z$: axial linear velocity $D_p$: diameter of flow path In fluid flow, when viscous forces are greater, a laminar flow occurs, in which elements within the fluid move parallel to each other in the direction of transport, and when inertial forces are greater, a turbulent flow occurs, in which elements within the fluid randomly move in the direction of transport. The Reynold's number is a value used to determine whether a flow in a pipe is a laminar flow or a turbulent flow. When the Reynold's number is about 2000 or less, it is determined to be the laminar flow, and when the Reynold's number is more than 2000, it is determined to be the turbulent flow. In other words, a lower Reynold's number of the fluid indicates that the flow is steady without turbulence.

In the hydrogenation method of a phthalate compound of the present invention, the Reynold's number of the liquid-phase raw material may be 1 or more, or 5 or more, or 10 or more, or 20 or more, and 100 or less, or 90 or less, or 80 or less, or 50 or less, or 30 or less.

When the Reynold's number of the liquid-phase raw material is as excessively low as less than 1, the acid value of the reaction product may become high. When the Reynold's number is as excessively high as more than 100, there is a problem in that the reactor size needs to be excessively increased or the reaction temperature needs to be excessively increased in order to obtain the desired level of yield. In this case, a production amount of by-products is increased, and as a result, an acid value of a product may be increased. In this point of view, it is preferable that the Reynold's number of the liquid-phase raw material is within the above-described range.

According to the present invention, since a uniform reaction may occur throughout the reactor, a load is uniformly applied to the catalyst in the upper/lower portions of the reactor, thereby maximizing the life-time of the catalyst, and the side reactions may be suppressed to remarkably increase the yield of the reactor, while the product may be controlled to have the low acid value. Further, since generation of a hot spot is suppressed due to the uniform reaction in the reactor, it is possible to control the amount of heat generated in the reactor without a separate heat control device.

In the present invention, a method of controlling the Reynold's number of the liquid-phase raw material introduced into the reactor is not particularly limited. For example, the Reynold's number of the liquid-phase raw material may be controlled by the temperature, the catalyst size, the reactor diameter, the amount of the liquid-phase raw material passing through the cross-sectional area, etc. In one embodiment of the present invention, the Reynold's number may be controlled by changing the reactor diameter, flow rate, etc., after determining the catalyst size, but the present invention is not limited thereto.

Further, in order to secure the above effects, the amount of hydrogen introduced into the reactor may be 3 mol or more, or 4 mol or more, or 7 mol or more, and 300 mol or less, or 100 mol or less, or 50 mol or less, or 30 mol or less with respect to 1 mol of the phthalate compound. If the amount of hydrogen is as too small at less than 3 mol with respect to 1 mol of the phthalate compound, a reaction conversion rate becomes low and thus it is difficult to obtain a conversion rate of 95% or more. If the amount is as too large at more than 300 mol, a retention time of droplets of the liquid-phase raw material in the reactor becomes short by hydrogen, and thus the conversion rate is lowered or by-products are increased, or the life-time of the catalyst may be rapidly decreased. In this point of view, it is preferable that the amount of hydrogen is within the above-described range.

The hydrogenation catalyst may include a transition metal as an active ingredient, and may preferably include one or more selected from the group consisting of ruthenium (Ru), palladium (Pd), rhodium (Rh), and platinum (Pt).

The hydrogenation catalyst may be used after being supported on a support. In this regard, as the support, any support known in the art may be used without limitation. Specifically, a support such as zirconia ($ZrO_2$), titania ($TiO_2$), alumina ($Al_2O_3$), silica ($SiO_2$), etc. may be used.

When the hydrogenation catalyst is supported on the support, the amount of the active ingredient of the hydrogenation catalyst may preferably be 3% by weight or less, 2% by weight or less, or 1% by weight or less, and 0.1% by weight or more, or 0.3% by weight or more with respect to 100% by weight of the support. If the amount of the hydrogenation catalyst is more than 3% by weight with respect to 100% by weight of the support, the reaction rapidly occurs on the catalyst surface, and during this process, side reactions also increase, which may cause a problem that the amount of by-products rapidly increases. If the amount is less than 0.1% by weight, the yield of the hydrogenation reaction may decrease due to an insufficient amount of the catalyst. Therefore, the above range is preferred.

In the present invention, the hydrogenation reaction conditions are not particularly limited. However, a reaction pressure may be, for example, 50 bar or more, or 100 bar or more, or 130 bar or more, and 220 bar or less, or 200 bar or less, or 180 bar or less. If the reaction pressure is less than 50 bar, there are various problems in that the reaction hardly occurs, and thus an excessive amount of the catalyst is consumed and the retention time becomes too long, and thus by-products increase and the acid value increases. If the reaction pressure exceeds 200 bar, excessive energy such as electricity is required during a process operation, and thus there is a problem in that a manufacturing cost of a facility such as a reactor may be greatly increased. Therefore, the above range is preferred.

Further, the reaction temperature may be 100° C. or higher, or 120° C. or higher, or 130° C. or higher, and 300° C. or lower, or 250° C. or lower, or 200° C. or lower. If the reaction temperature is lower than 100° C., there is a problem in that the reaction rate is too slow and thus the reaction may not smoothly occur. If the reaction temperature is higher than 300° C., by-products are rapidly increased and the acid value of a product may be greatly increased. Further, the life-time of the catalyst may be also influenced. Therefore, the above range is preferred.

By the hydrogenation reaction, an aromatic ring of the phthalate compound is hydrogenated to be converted into the cyclohexane dicarboxylate compound corresponding thereto.

After the reaction is terminated, the produced liquid-phase hydrogenation product and unreacted gas-phase raw material are separated from each other. The separated gas-phase raw material may be recirculated in the hydrogenation process. The recovered hydrogenation product may be finally separated through a decompression and cooling process.

Through the hydrogenation method according to the present invention, the hydrogenation product thus prepared and separated may have an acid value of 0.3 KOHmg/g or less, 0.2 KOHmg/g or less, or 0.17 KOHmg/g or less. As the hydrogenation product has a lower acid value, quality of the product is much better, and thus there is no restriction on the lower limit. For example, the acid value may be 0.01 KOHmg/g or more, or 0.03 KOHmg/g or more. In this regard, the acid value range suggested above does not mean a heating acid value. The acid value is the weight (mg) of potassium hydroxide (KOH) needed to neutralize acids included in 1 g of a sample, and the acid value may be determined by titrating a sample solution with a 0.1 N alcoholic KOH solution.

Further, after heating the hydrogenation product, the acid value may be 0.4 KOHmg/g or less, 0.3 KOHmg/g or less, or 0.25 KOHmg/g or less. As the acid value after heating is lower, quality of the product is much better, and thus there is no restriction on the lower limit. For example, the acid value after heating may be 0.01 KOHmg/g or more, 0.05 KOHmg/g or more, or 0.1 KOHmg/g or more.

In this regard, the acid value after heating the hydrogenation product is a value obtained by maintaining the hydrogenation product prepared and separated by the method of the present invention at 125° C. for 3 h, and then titrating and calculating in the same manner as the above method of measuring the acid value.

According to the hydrogenation method of the present invention, in which the liquid-phase raw material is introduced by controlling the Reynold's number thereof, side reactions other than the hydrogenation reaction are suppressed, and as a result, production of acidic by-products is reduced, and the hydrogenation product exhibits the low acid value as above, thereby obtaining a high-purity and high-quality product.

The drawing illustrates a hydrogenation reaction apparatus used in the hydrogenation method of the present invention.

Referring to the drawing, the hydrogenation reaction apparatus may be composed of heat exchangers A and B, a reactor C, a gas-liquid separator D, etc.

The heat exchangers A and B function to heat a gas-phase raw material 1 and a liquid-phase raw material 3 before introducing them into the reactor C, and may be omitted, as needed.

The gas-phase raw material 2 and the liquid-phase raw material 4 are introduced into a pipe-type reactor C, of which interior is filled with a hydrogenation catalyst, and the hydrogenation reaction proceeds. The reactor may further include an outer jacket for heat removal in order to control the reaction heat. In this regard, the gas-phase raw material 2 may be fed into an upper portion or a lower portion of the reactor, and the liquid-phase raw material 4 may be fed into the upper portion of the reactor.

A reaction mixture 5 discharged from the reactor C is transferred to the gas-liquid separator D, wherein a liquid-phase reaction product 7 and an unreacted gas-phase 6 are separated from each other. The separated reaction product 7 may be recovered and further subjected to a purification process, and the unreacted gas-phase 6 is circulated in order to be discharged or recycled.

However, a position of each of the devices shown in the drawing FIG. 1 may be changed, and if necessary, other devices that are not shown in the drawing may be included. Therefore, the hydrogenation method according to the present invention is not limited to the apparatus and the process sequence shown in to the drawing.

According to the above-described hydrogenation method of the present invention, side reactions are suppressed, and thus the hydrogenation product may be controlled to have a low acid value, while the catalytic activity is improved and life-time is extended. As a result, quality of a product may be improved and economic efficiency of a commercial process may be increased.

The hydrogenated phthalate or terephthalate compound prepared as above may be usefully applied as a plasticizer. Specifically, a plasticizer including the phthalate or terephthalate compound may be applied to products such as stabilizers, paints, inks, liquid-phase blowing agents (Masterbatches), adhesives, etc.

The hydrogenated phthalate or terephthalate compound prepared according to the present invention has excellent purity and a low acid value, and thus has excellent quality as a plasticizer. Therefore, it may be suitably used as a plasticizer for a resin selected from ethylene vinyl acetate, polyethylene, polypropylene, polyvinyl chloride, polystyrene, polyurethane, polybutadiene, silicone, thermoplastic elastomers, and copolymers thereof.

A resin composition including the phthalate or terephthalate compound prepared according to the present invention as a plasticizer and the above-described resin may be used in a variety of products. For example, the resin composition may be used in the preparation of food packaging films (e.g., wraps), industrial films, compounds, deco sheets, deco tiles, soft sheets, hard sheets, wires and cables, wallpaper, foam mats, artificial leather, flooring materials, tarpaulins, gloves, sealants, refrigerator gaskets, hoses, medical devices, geogrids, mesh tarpaulins, toys, stationery, insulating tapes, clothing coatings, PVC labels used for clothing or stationery, bottle cap liners, stoppers for industrial or other purposes, artificial baits, parts (e.g., sleeves) in electronic devices, automobile interior materials, adhesives, and coating agents, but is not limited thereto.

Hereinafter, actions and effects of the present invention will be described in more detail with reference to specific examples of the present invention. However, these examples are for illustrative purposes only, and the scope of the present invention is not intended to be limited thereby.

EXAMPLE

Example 1

Dioctyl terephthalate (DOTP) with purity of 99% as a liquid-phase raw material and hydrogen as a gas-phase raw material were introduced into a reactor, and hydrogenation was allowed at a reaction pressure of 110 bar and a reaction temperature of 150° C.

A mass flow rate of DOTP was 9.6 kg/h, and hydrogen was introduced so that a molar ratio of hydrogen/DOTP became 10 mol. Further, a volume flow ratio of hydrogen and DOTP was 5:1, and the temperature and pressure at the time of introducing hydrogen were 140° C. and 150 bar, respectively, and the temperature and pressure at the time of introducing DOTP were 140° C. and 150 bar, respectively.

Further, the Reynold's number of the liquid-phase raw material introduced into the reactor was set to 84.9, followed by operating. Here, the Reynold's number is a value calculated by the following Equation 1.

$$\text{Reynold's No.}(N_{Re}) = \frac{\rho \times u_z \times D_p}{\mu} \qquad \text{[Equation 1]}$$

μ: viscosity ρ: density $u_z$: axial linear velocity $D_p$: diameter of flow path The reactor was in the form of a single tube, and a length of a portion of the tube filled with the catalyst was a total of 3.0 m. The hydrogenation reaction was performed without an outer jacket for heat removal.

The catalyst used in the reactor was a ruthenium (Ru) catalyst, which was prepared by using 0.5% by weight of ruthenium with respect to 100% by weight of a support, and the reactor was a cylinder type with a diameter of 3 mm and a height of 3 mm.

Example 2

The hydrogenation reaction was performed in the same manner as in Example 1, except that the Reynold's number of the liquid-phase raw material was 8.5.

Example 3

The hydrogenation reaction was performed in the same manner as in Example 1, except that the Reynold's number of the liquid-phase raw material was 1.3.

Comparative Example 1

The hydrogenation reaction was performed in the same manner as in Example 1, except that the reaction temperature was 200° C. and the Reynold's number of the liquid-phase raw material was 124.

Comparative Example 2

The hydrogenation reaction was performed in the same manner as in Example 1, except that the Reynold's number of the liquid-phase raw material was 0.1.

Comparative Example 3

The hydrogenation reaction was performed in the same manner as in Example 1, except that the Reynold's number of the liquid-phase raw material was 124.

However, in this case, the reaction conversion rate was as low as 48.5%, and the reaction did not sufficiently proceed, and thus was not suitable for comparison of the acid value of the product.

Experimental Example

With respect to the hydrogenation reactions of Examples 1 to 3 and Comparative Examples 1 to 4, conversion rates, contents of by-products, acid values of hydrogenation products, acid values of hydrogenation products after heating, and life-time of the catalysts were evaluated.

Analyses of the reaction products and by-products were performed using a GC instrument (Agilent 6890 and 7890B) generally used in the analysis of organic materials, a sample prepared by mixing 0.25 mL of a liquid-phase analysis sample with 1 mL of acetone was injected into the GC instrument, and the analysis time was set to a total of 34 min, followed by performing analysis.

The acid value of the hydrogenation product is a value calculated by the following Equation 2, after titrating, with a KOH reagent, the hydrogenation product obtained by separating unreacted gas-phase raw material from the reaction mixture.

$$\text{Acid value} = \frac{0.561 \times \alpha \times \beta}{\delta} \qquad \text{[Equation 2]}$$

α: Consumption amount of titration reagent (KOH), β: 1.00, δ: Feeding amount of sample (hydrogenation product)

The acid value after heating is a value obtained in the same manner as the above method of measuring the acid value of the hydrogenation product, after maintaining the hydrogenation product separated from the reaction mixture at 125° C. for 3 h.

The life-time of the catalyst is a value calculated based on an initial reaction conversion rate ($x_0$) and a conversion rate ($X_1$) after operating for 5 days.

The evaluation results are summarized in Table 1 below.

TABLE 1

| Experimental Example | | Example 1 | Example 2 | Example 3 | Comparative Example 1 | Comparative Example 2 |
|---|---|---|---|---|---|---|
| Reynold's number of liquid-phase | | 84.9 | 8.5 | 1.3 | 124 | 0.10 |
| Catalyst | | Ru 0.5 | Ru 0.5 | Ru 0.5 | Ru 0.5 | Ru 0.5 |
| Conversion rate | % | 85.5% | 98.5% | 99.5% | 84.5% | 99.9% |
| By-products | wt % | 0.68% | 0.16% | 0.24% | 1.54% | 0.90% |
| Acid value | KOH mg/g | 0.154 | 0.030 | 0.070 | 0.413 | 0.229 |
| Acid value after heating | KOH mg/g | 0.225 | 0.112 | 0.147 | 0.485 | 0.276 |
| Life-time of catalyst | $(X_0 - X_1)/X_0$ | 0.94 | 0.99 | 0.98 | 0.64 | 0.75 |

Referring to Table 1, when the Reynold's numbers of the gas-phase and liquid-phase raw materials satisfy the range of the present invention, as in Examples 1 to 3, an excellent conversion rate of 85% or more was observed, whereas the production amount of by-products as low as 0.7% or less was observed. As described, due to the reduced amount of by-products, the hydrogenation product separated from the reaction mixture showed a very low acid value of 0.16 KOHmg/g or less, and its acid value after heating was maintained at 0.3 KOHmg/g or less. Further, the problem of catalytic activity loss by by-products was solved, and the life-time of the catalyst was greatly extended.

In contrast, Comparative Examples 1 and 2, in which the Reynold's number of the gas-phase or liquid-phase raw material was set outside the range of the present invention, showed very high amounts of by-products, as compared with Examples 1 to 3. As a result, the acid value of the hydrogenation product and its acid value after heating were high, and the life-time of the catalyst was also rapidly reduced, as compared with those of the examples.

The above results suggest that, in the hydrogenation method of a phthalate compound, when the Reynold's numbers of the gas-phase and liquid-phase raw materials introduced into the reactor are controlled within the range of the present invention, side reactions may be greatly suppressed to increase quality of the hydrogenation product, and the life-time of the catalyst may be increased to improve productivity and economic efficiency.

REFERENCE NUMERALS a, b: Heat exchanger
c: Reactor
d: Gas-liquid separator
1, 2: Gas-phase raw material
3, 4: Liquid-phase raw material
5: Reaction mixture
6: Unreacted gas-phase
7: Liquid-phase reaction product

The invention claimed is:

1. A hydrogenation method of a phthalate compound, introducing a gas-phase raw material including hydrogen and a liquid-phase raw material including the phthalate compound into a reactor; and
performing a reaction of the hydrogen and the phthalate compound in the presence of a hydrogenation catalyst to prepare a hydrogenated phthalate compound,
wherein,
the phthalate compound is one or more selected from the group consisting of phthalate, terephthalate, and isophthalate,
the amount of hydrogen introduced into the reactor is 3 mol to 300 mol with respect to 1 mol of the phthalate compound,
the Reynold's number of the liquid-phase raw material in the reactor is 1 to 100,
the acid value of the hydrogenated phthalate compound is 0.3 KOHmg/g or less.

2. The hydrogenation method of a phthalate compound of claim 1, wherein the acid value of the hydrogenated phthalate compound is 0.2 KOHmg/g or less.

3. The hydrogenation method of a phthalate compound of claim 1, wherein the acid value of the hydrogenated phthalate compound is 0.4 KOHmg/g or less after heating.

4. The hydrogenation method of a phthalate compound of claim 1, wherein the acid value of the hydrogenated phthalate compound is 0.3 KOHmg/g or less after heating.

5. The hydrogenation method of a phthalate compound of claim 1, wherein the gas-phase raw material is fed into an upper portion or a lower portion of the reactor, and the liquid-phase raw material is fed into an upper portion of the reactor.

6. The hydrogenation method of a phthalate compound of claim 1, wherein the active ingredient of the hydrogenation catalyst is one or more selected from the group consisting of ruthenium (Ru), rhodium (Rh), palladium (Pd), and platinum (Pt).

7. The hydrogenation method of a phthalate compound of claim 1, wherein the hydrogenation catalyst includes 3% by weight or less of the catalyst active ingredient with respect to 100% by weight of a support.

* * * * *